United States Patent [19]

Lödige et al.

[11] 4,062,646

[45] Dec. 13, 1977

[54] PROCESS FOR STERILIZING LOOSE MATERIAL

[76] Inventors: Wilhelm Lödige, Elsenerstrasse 9c; Fritz Lödige, Leuschnerstrasse 12; Josef Lücke, Im Lohfeld 15, all of D-479 Paderborn, Germany

[21] Appl. No.: 733,699

[22] Filed: Oct. 19, 1976

Related U.S. Application Data

[62] Division of Ser. No. 571,699, April 25, 1975, Pat. No. 3,994,685.

[30] Foreign Application Priority Data

May 11, 1974   Germany ............................ 2422907

[51] Int. Cl.² .......................... A21D 6/00; A23L 3/16; A23L 3/34; A61L 1/00
[52] U.S. Cl. .......................................... 21/56; 21/57; 21/58; 21/59; 426/521
[58] Field of Search ....................................... 21/56–59, 21/91–96; 426/521

[56] References Cited

U.S. PATENT DOCUMENTS

| | | | |
|---|---|---|---|
| 2,086,338 | 7/1937 | Sodergreen | 21/56 |
| 3,088,179 | 5/1963 | Leuthner | 21/58 |
| 3,232,770 | 2/1966 | Schack et al. | 21/56 |
| 3,721,527 | 3/1973 | Lodige et al. | 21/93 |
| 3,767,362 | 10/1973 | Griffin et al. | 21/57 |
| 3,888,167 | 6/1975 | Starkie | 99/355 |
| 3,992,148 | 11/1976 | Shore et al. | 21/91 |

*Primary Examiner*—Morris O. Wolk
*Assistant Examiner*—Bradley Garris
*Attorney, Agent, or Firm*—Donald D. Jeffery

[57] ABSTRACT

Two-stage process for sterilizing loose material, such as flour, cocoa, feedstuffs, fillers for cosmetics and pharmaceuticals, and mould cultures, by means of sterilizing agents, such as superheated steam. In the first stage the loose material is vigorously mixed with the sterilizing agent by means of a mechanical agitator, while being brought to the sterilization temperature. In the second stage the loose material is allowed to remain virtually stationary for a predetermined length of time at the sterilization temperature.

6 Claims, 1 Drawing Figure

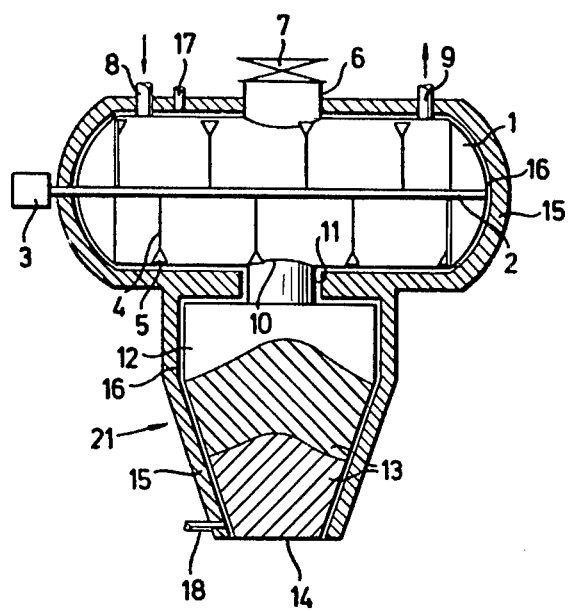

PROCESS FOR STERILIZING LOOSE MATERIAL

This is a division, of application Ser. No. 571,699, filed April 25, 1975, now U.S. Pat. No. 3,994,685.

BACKGROUND OF THE INVENTION

1. Field of the Invention

This invention relates to a process for sterilizing loose material by means of sterilizing agents, such as superheated steam, which are positively mixed with the continuously agitated material with exclusion of air to heat the material to the sterilization temperature. The invention also relates to an apparatus for carrying out such a process, comprising a sterilization container in which an agitator is rotatably mounted to agitate the material to be sterilized and which is provided with means for discharging and introducing sterilizing agents.

2. Description of the Prior Art

It has become increasingly customary to sterilize loose materials such as flour, cocoa, feedstuffs, fillers for cosmetics and pharmaceuticals and mould cultures, so that completely new fields of application have opened up for sterilisation. In particular, sterilisation must be adapted to high throughput rates for such bulk goods.

Various continuously operating apparatus for sterilizing loose material are already known which contain stationary or movable baffles and inserts to ensure that the product which is being treated cannot leave the apparatus until it has been in it for the minimum length of time required for sterilisation. In spite of elaborate constructional measures, however, so-called short circuits cannot be prevented in practice, that is to say portions of the products being treated are liable to pass too rapidly through the apparatus so that they do not stay in it for the minimum time prescribed for sterilisation. If portions of the product are left unsterilized, the whole quantity of the product is, of course, unsterile since the non-sterilized portions contaminate the remainder. It is also difficult to empty such apparatus completely and clean them.

For batchwise sterilisation of loose material using steam or gas as the sterilizing agent, it is known to loosen up the material vigorously and agitate it so as to fluidize it and at the same time add the sterilizing agent and thereafter discharge the sterilizing agent from the sterilized material at subatmospheric pressure while the material continues to be vigorously agitated and loosened up (German Offenlegungsschrift 1,642,087). To ensure complete sterilisation, the material must be kept at the sterilisation temperature for a given time which varies according to the temperature. The higher the sterilisation temperature employed, the shorter is the necessary sterilisation time. Since, however, there is a limit to the sterilisation temperature which can be employed, the material must be kept in the sterilisation zone for a comparatively long period and at the same time thoroughly loosened up and agitated. Due to its comparatively long residence time in the structurally complicated dynamic sterilizer, the material is then liable to suffer mechanical damage.

SUMMARY OF THE INVENTION

It is an object of the present invention to reduce the effort required for sterilisation of loose materials and particularly the mechanical effort and hence to reduce the mechanical stress to which the loose material is subjected.

It has been found that in order to achieve economical and yet reliable sterilisation of loose material, it is essential that the sterilizing agent should briefly come into contact with every particle of the loose material so that the material is completely and as rapidly as possible heated to a uniform sterilisation temperature. All that is thereafter required is to keep the material at the sterilisation temperature for the necessary sterilisation time.

The solve the given problem in the light of this finding, the invention proposes that in a process of the type described above, the material to be sterilized is kept practically stationary in a post-sterilisation zone at the sterilisation temperature for a predetermined length of time after it has been heated to the sterilisation temperature and, if desired, after removing the sterilizing agent from the material.

Sterilisation is therefore virtually carried out as a two stage process in which the material to be sterilized is rapidly and uniformly heated to the desired sterilisation temperature in the first stage and kept at the sterilisation temperature for the necessary length of time in the second stage. The material to be sterilized is vigorously mixed with sterilizing agent with the aid of a mechanical agitator to bring it to the sterilisation temperature, but in the post-sterilisation zone it is sufficient to ensure that the temperature of the material does not drop below the sterilisation temperature. No mechanical devices such as stirrers or mixers are therefore required in the post-sterilisation zone, and the energy consumption and wear and tear are therefore reduced accordingly and there is no further risk of mechanical damage to the material.

In the post-sterilisation zone, the temperature is maintained mainly by preventing loss of heat by radiation. In addition, external heating may also be applied. The temperature of the material will then not drop below the desired temperature even in the interior of the mass of material.

The sterilized material is preferably removed continuously from the post-sterilisation zone, regardless of whether the treatment with sterilizing agent in the main sterilisation zone is carried out continuously or batchwise. The residence time of sterilized material in the post-sterilisation zone can in this way be controlled as desired.

It is particularly desirable to mix the material batchwise with sterilizing agent to heat it to the sterilisation temperature, that is to say after the material has been mixed with sterilizing agent and thus heated to the sterilisation temperature, it is also introduced batchwise into the post-sterilisation zone but removed continuously from this zone.

Furthermore, to solve the given problem in an apparatus of the type described above, it is proposed to provide a second chamber downstream of the chamber which contains the stirrer or mixer, in which second chamber the material which has been heated to the sterilisation temperature is kept under sterilisation conditions for a predetermined length of time before it is removed from the apparatus.

The first chamber preferably consists of any mixing vessel in which a mixing device is installed whereas the second chamber is a silo-type of container which is attached to the discharge opening of the mixing vessel and itself has a discharge opening at the bottom. When the material has been heated to the required temperature by the sterilizing agent, it is discharged, for example from the mixing vessel into the second chamber which is provided for post-sterilisation. It is generally introduced batchwise into the second chamber and it remains there for the necessary sterilisation time. The completely sterilized material is then discharged from the second chamber, preferably continuously.

The capacity of the post-sterilizer provided for the post-sterilisation treatment is preferably equal to or greater than the capacity of the mixing vessel so that a number of batches of material from the mixing vessel can be kept in the post-sterilisation vessel for the necessary post-sterilisation time before the completely sterilized material is removed continuously. The capacity of the post-sterilizer need not necessarily be greater than the capacity of the mixing and sterilizing vessel preceding it, the necessary capacity depending rather on the extent to which the mixing vessel is filled.

To ensure continuous and uniform removal of completely sterilized material without any mechanical conveyor devices, another feature of the invention provides that the post-sterilizer is a mass flow bin from which the sterilized material pours out of the opening at the bottom in such a manner that the various batches of sterilized material which are stacked in layers above one another in the bin leave it uniformly, that is to say layer by layer. This ensures that every portion of material remains for the same length of time in the post-sterilizer and no portions can be short circuited.

To ensure that the material in the post-sterilisation zone will be kept at the sterilisation temperature, the post-sterilizer is thermally insulated, i.e. it is protected against loss of heat by radiation, as is also the mixing vessel preceding it. If no heat can radiate outwards, the mass of sterilized material will not cool down. However, since heat losses cannot always be completely prevented, another feature of the invention provides that both the post-sterilizer and the mixing vessel preceding it are adapted to be heated externally to compensate for the heat loss. If the layer of sterilized material adjacent to the wall of the post-sterilizer is kept at the sterilisation temperature, no heat will be lost from the interior of the mass of material by radiation and therefore once the material has been heated through completely to the sterilisation temperature, it can be kept at this temperature for a considerable period with minimum energy consumption. The sterilized material does not begin to cool down until it has left the apparatus.

BRIEF DESCRIPTION OF THE DRAWING

The drawing is a diagrammatic longitudinal section through an embodiment of a sterilisation apparatus according to the invention.

DESCRIPTION OF THE PREFERRED EMBODIMENT

A preferred embodiment of the apparatus comprises a cylindrical container 1, with a horizontal axis in which a shaft 2 is mounted. The shaft 2 is driven by a motor 3 and has radial arms 4 attached to it along its length and over its circumference, with mixing devices 5 attached to the ends of the arms.

A feed hopper connection 6 through which the material to be sterilized is introduced into the container 1 is provided at the top of the container and may be closed by a cover 7. A sterilizing agent such as steam or a gas can be introduced into the container through a pipe connection 8 and discharged from the container 1 through a pipe connection 9.

Sterilisation of the loose material is carried out in container 1. To achieve this, the loose material is vigorously agitated and loosened up by means of the rotating mixing device and thereby mixed with the sterilizing agent introduced into container 1. Every particle of loose material in container 1 is thereby heated to the sterilisation temperature within a very short time. The sterilizing agent may be withdrawn through the pipe connection 9 and the heated material may be discharged from the container 1.

To empty the container 1, an aperture 10 covered with a closure flap (not shown) as situated at the bottom of the container 1 and opens into a downpipe 11 which in the illustrated embodiment opens into a mass flow bin 12 which is situated underneath the container 1 and serves a post-sterilizer. In this mass flow container, which has no mechanical inserts, the material which has been heated to the sterilisation temperature remains virtually stationary in the form of layers 13 stacked above one another for the remainder of the required sterilisation time, the post-sterilizer being kept under sterilisation conditions. After expiry of the required post-sterilisation time, the sterilized material is continuously removed through an outlet 14 at the lower end of the mass flow bin 12. The sterilized material also leaves the post-sterilizer uniformly, that is to say the various layers 13, which may, for example, correspond to the individual batches introduced into the mass flow bin 12 from the container 1 are emptied evenly one after another. The discharge aperture 14 may be provided with a closure member (not shown).

In the illustrated embodiment, the container 1 in which sterilisation begins and the mass flow bin 12 which serves as post sterilizer are combined to form one structural unit and covered with an insulating jacket 15 which is spaced apart from the external surface of the container 1, downpipe 11 and mass flow bin 12 so as to leave a cavity 16 between the external wall of the unit and the insulating jacket. The jacket therefore serves as a double jacket for a heating medium. An inlet pipe connection 17 opens into the cavity 16 for the introduction of a heating medium such as steam, and an outlet connection 18 is provided to remove the cooled heating medium as condensate. Baffle plates (not shown) may be arranged within the cavity 16 to guide the flow of heating medium. If desired, the heating medium may flow through the cavity 16 in the reverse direction, i.e. from 18 to 17.

In the illustrated embodiment, the container 1 which forms the sterilizer and the mass flow bin 12 which forms the post-sterilizer are combined to form a unit which may be provided with legs or some other framework to support it on a base, and in this form it may be transported to the required site as one structural unit. Alternatively, the sterilizer and post-sterilizer may be set up separately from each other, in which case the material may be transferred from the container 1 to the mass flow bin 12 for example through a heat insulated, encapsulated conveyor device such as a conveyor screw.

As the sterilized material is continuously removed through the discharge aperture 14, the layers 13 in the mass flow bin 12 gradually sink so that each layer reaches the emptying zone after expiry of the necessary sterilisation time and can be removed. This downward movement is the only movement carried out by the material or product in the post-sterilizer so that the material is not subjected to any mechanical damage during the period of post-sterilisation. Reliable sterilisation and controlled destruction of bacteria in loose materials of all kinds can thus be achieved with the simplest apparatus and under the most careful treatment of the loose material.

Although in the example described above the loose material is sterilized batchwise in the first sterilisation stage and continuously removed from the post-sterilisation zone, the heating of the material to the sterilisation temperature in the first treatment stage may also be carried out continuously.

What is claimed is:

1. A process for the sterilization of loose material by means of a sterilizing agent and heat comprising the steps of continuously agitating the material, positively mixing said sterilizing agent with the continuously agitated material, heating said material to a sterilization temperature, and after said material has been heated to the sterilization temperature, allowing said material to remain virtually stationary for a predetermined length of time sufficient to sterilize said material at the sterilization temperature in a post-sterilization zone.

2. The process according to claim 1, wherein said sterilizing agent is superheated steam.

3. The process according to claim 1, wherein said sterilizing agent is removed from said material before the step of keeping said material stationary.

4. The process according to claim 1, wherein the sterilized material is continuously discharged from said post-sterilization zone.

5. The process according to claim 1, wherein said sterilizing agent is superheated steam and said material to be sterilized is heated to the sterilization temperature during the step of mixing said steam with said material, and wherein said steam and said material are mixed together in a batchwise fashion.

6. A process for the sterilization of loose material by means of a sterilizing agent and heat comprising the steps of continuously agitating the material, mixing said material batchwise with said sterilizing agent while heating said material to a sterilization temperature, and thereafter keeping said material virtually stationary for a predetermined length of time sufficient to sterilize said material at the sterilization temperature in a post-sterilization zone, and discharging said material continuously from said post-sterilization zone.

* * * * *